United States Patent
Takahashi et al.

(10) Patent No.: US 7,116,752 B2
(45) Date of Patent: Oct. 3, 2006

(54) DIAGNOSTIC X-RAY SYSTEM

(75) Inventors: Tooru Takahashi, Otawara (JP); Takashi Kurihara, Otawara (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/659,310

(22) Filed: Sep. 11, 2003

(65) Prior Publication Data

US 2004/0066897 A1    Apr. 8, 2004

Related U.S. Application Data

(63) Continuation of application No. PCT/JP02/03210, filed on Mar. 29, 2002.

(30) Foreign Application Priority Data

Mar. 29, 2001 (JP) .............................. 2001-097116

(51) Int. Cl.
*G01N 23/04* (2006.01)
(52) U.S. Cl. ...................... 378/62; 378/98.7
(58) Field of Classification Search .............. 378/4–20, 378/42, 62, 98.7
See application file for complete search history.

(56) References Cited

U.S. PATENT DOCUMENTS 6,175,614 B1 * 1/2001 Jensen et al. ............... 378/98.7

FOREIGN PATENT DOCUMENTS

| EP | 0 276 170 | 7/1988 |
|----|-----------|--------|
| JP | 61-269098 | 11/1986 |
| JP | 1-146564  | 6/1989 |
| JP | 3-209980  | 9/1991 |
| JP | 4-207366  | 7/1992 |
| JP | 5-264788  | 10/1993 |
| JP | 9-234198  | 9/1997 |
| JP | 10-228995 | 8/1998 |
| JP | 11-276462 | 10/1999 |
| JP | 2000-245721 | 9/2000 |

* cited by examiner

*Primary Examiner*—Courtney Thomas
(74) *Attorney, Agent, or Firm*—Oblon, Spivak, McClelland, Maier & Neustadt, P.C.

(57) ABSTRACT

A region affected by X-ray beam limiting within a fluoroscopic image is specified based on position information on beam limiting by an X-ray beam limiting device. A judgment is made as to whether the region affected superposes a first brightness measuring region (region of interest) within the X-ray fluoroscopic image, and when superposition is not judged, automatic brightness control is performed based on the first brightness measuring region. When superposition is judged, the first brightness measuring region is transformed, and automatic brightness control is performed with reference to a second automatic brightness measuring region that does not superpose the region affected.

9 Claims, 5 Drawing Sheets

DIAGNOSTIC X-RAY SYSTEM

CROSS-REFERENCE TO RELATED APPLICATIONS

This is a Continuation Application of PCT Application No. PCT/JP02/03210, filed Mar. 29, 2002, which was not published under PCT Article 21(2) in English.

This application is based upon and claims the benefit of priority from the prior Japanese Patent Application No. 2001-097116, filed Mar. 29, 2001, the entire contents of which are incorporated herein by reference.

BACKGROUND OF THE INVENTION

1. Field of the Invention

The present invention relates to a diagnostic X-ray system with automatic brightness control processing.

2. Description of the Related Art

A diagnostic X-ray system is an imaging apparatus that displays variance in strength of X-rays passing through the interior of a subject as a gray-scale image, and includes various types adapted for specific use in diagnosis, treatment, etc. Means for turning a transmission X-ray image into a visible image is roughly divided into two methods: imaging and fluoroscopy. For example, a diagnostic X-ray system adopting fluoroscopy has excellent immediacy in that an acquired X-ray image can be observed in real time as a moving picture on a TV monitor.

A diagnostic X-ray system adopting fluoroscopy or imaging (hereinafter, referred to as the diagnostic X-ray system) is generally furnished with a function referred to as automatic brightness control. This is a function that maintains constant brightness for an X-ray fluoroscopic image being displayed through automatic control by changing X-ray loading factors.

Figure 7:
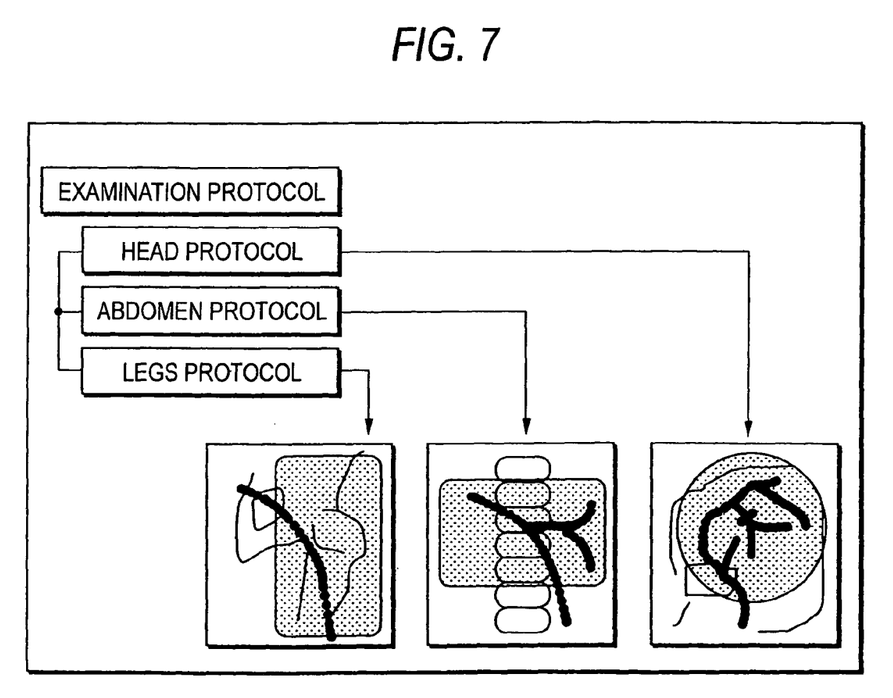
FIG. 7 is a view used to explain a function that automatically sets a brightness measuring region for each region.

FIG. 7 is a view used to explain the automatic brightness control function in a conventional diagnostic X-ray system, showing X-ray fluoroscopic images displayed on a TV monitor.

Figure 1:
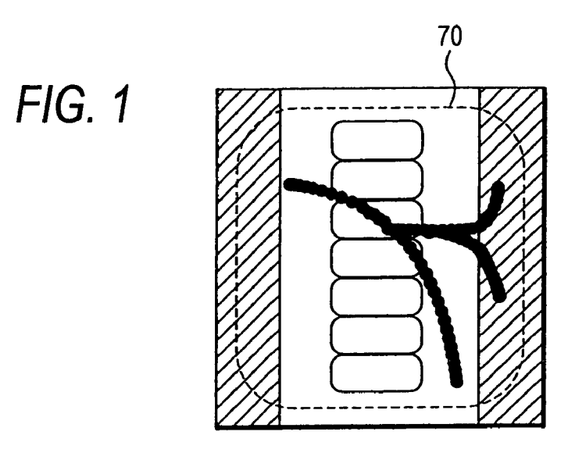
FIG. 1 is a view used to explain conventional automatic brightness control processing.

According to the conventional diagnostic X-ray system, average brightness of a brightness measuring region 70 within an X-ray fluoroscopic image, for example, as shown in FIG. 1 is computed by a brightness measuring apparatus (for example, an apparatus that measures a level of a photo-multiplier and a video level). Then, automatic brightness control is performed by discriminating between light and dark across the brightness measuring region 70, then determining X-ray loading factors so that appropriate brightness is achieved, and feeding back the X-ray loading factors to an X-ray generating system.

Incidentally, with the aim to prevent a subject from being submitted to overexposure, to make a displayed image easier to see, etc, an X-ray beam radiated from an X-ray generating system is occasionally limited by an X-ray beam limiting device during diagnosis using the diagnostic X-ray system. In this case, an X-ray fluoroscopic image is affected by such beam limiting, which in turn limits an image region as shown in FIG. 1.

However, because average brightness is computed based on the brightness measuring region 70 by the aforementioned conventional automatic brightness control function, when the brightness measuring region 70 is subjected to such beam limiting as shown in FIG. 1, brightness control is performed while including a region affected by the beam limiting. This results in brightness control such that brightens the X-ray fluoroscopic image exceedingly, and thereby makes it impossible to determine X-ray loading factors that can provide optimal brightness.

In addition, a region of interest in diagnosis generally differs from region to region. Nevertheless, the brightness measuring region 70 in the conventional diagnostic X-ray system is of specific shape and size regardless of an object to be imaged (region). Hence, there may be a case that the brightness measuring region 70 does not correspond to a region of interest for a given region being displayed, which makes adequate brightness control corresponding to the given region infeasible.

The invention was devised in view of the foregoing, and therefore has an object to provide a diagnostic X-ray system that is unsusceptible to X-ray beam limiting and capable of performing adequate brightness control processing corresponding to a region to be examined with ease.

BRIEF SUMMARY OF THE INVENTION

That is to say, one aspect of the invention provides a diagnostic X-ray system, including: an X-ray generating unit that radiates an X-ray to a subject at a predetermined X-ray loading factor; a beam limiting unit that limits a radiation region of the X-ray through beam limiting; an image generating unit that generates an image of a predetermined size based on the X-ray passing through an interior of a body of the subject; a brightness computing unit that computes brightness related to a predetermined region within the image; a controller that determines an X-ray loading factor based on the brightness computed in the brightness computing unit and performs feedback control of the X-ray loading factor with respect to the X-ray generating unit; and a judging unit that judges whether a region corresponding to the beam limiting superposes the predetermined region within the image, wherein when the judging unit judges superposition, the brightness computing unit transforms the predetermined region to a given region that does not superpose the region corresponding to the beam limiting, and computes brightness based on the given region.

Another aspect of the invention provides a diagnostic X-ray system, including: an X-ray generating unit that radiates an X-ray to a subject at a predetermined X-ray loading factor; a beam limiting unit that limits a radiation region of the X-ray through beam limiting; an image generating unit that generates an image of a predetermined size based on the X-ray passing through an interior of a body of the subject; a brightness computing unit that computes brightness related to a first region within the image when X-ray fluoroscopy is performed, and computes brightness related to a second region within the image when X-ray imaging is performed; a controller that determines an X-ray loading factor based on the brightness computed in the brightness computing unit and performs feedback control of the X-ray loading factor with respect to the X-ray generating unit; and a judging unit that judges whether a region corresponding to the beam limiting superposes the first region or the second region within the image, wherein: when the judging unit judges that the region corresponding to the beam limiting superposes the first region in the X-ray fluoroscopy, the brightness computing unit transforms the first region to a third region that does not superpose the region corresponding to the beam limiting, and computes brightness based on the third region; when the judging unit judges that the region corresponding to the beam limiting does not superpose the second region in the X-ray imaging, the brightness computing unit computes brightness based on the second region; and when the judging unit judges that the region corresponding to the beam limiting superposes the second region in the X-ray imaging, the brightness computing unit transforms the second region to the third region and computes brightness based on the third region.

DETAILED DESCRIPTION OF THE INVENTION

The following description will describe embodiments of the invention with reference to the drawings. The invention is applicable to both a fluoroscopic diagnostic X-ray system and an imaging diagnostic X-ray system (or a diagnostic X-ray system picking up an image in both a fluoroscopic mode and an imaging mode).

Figure 2:
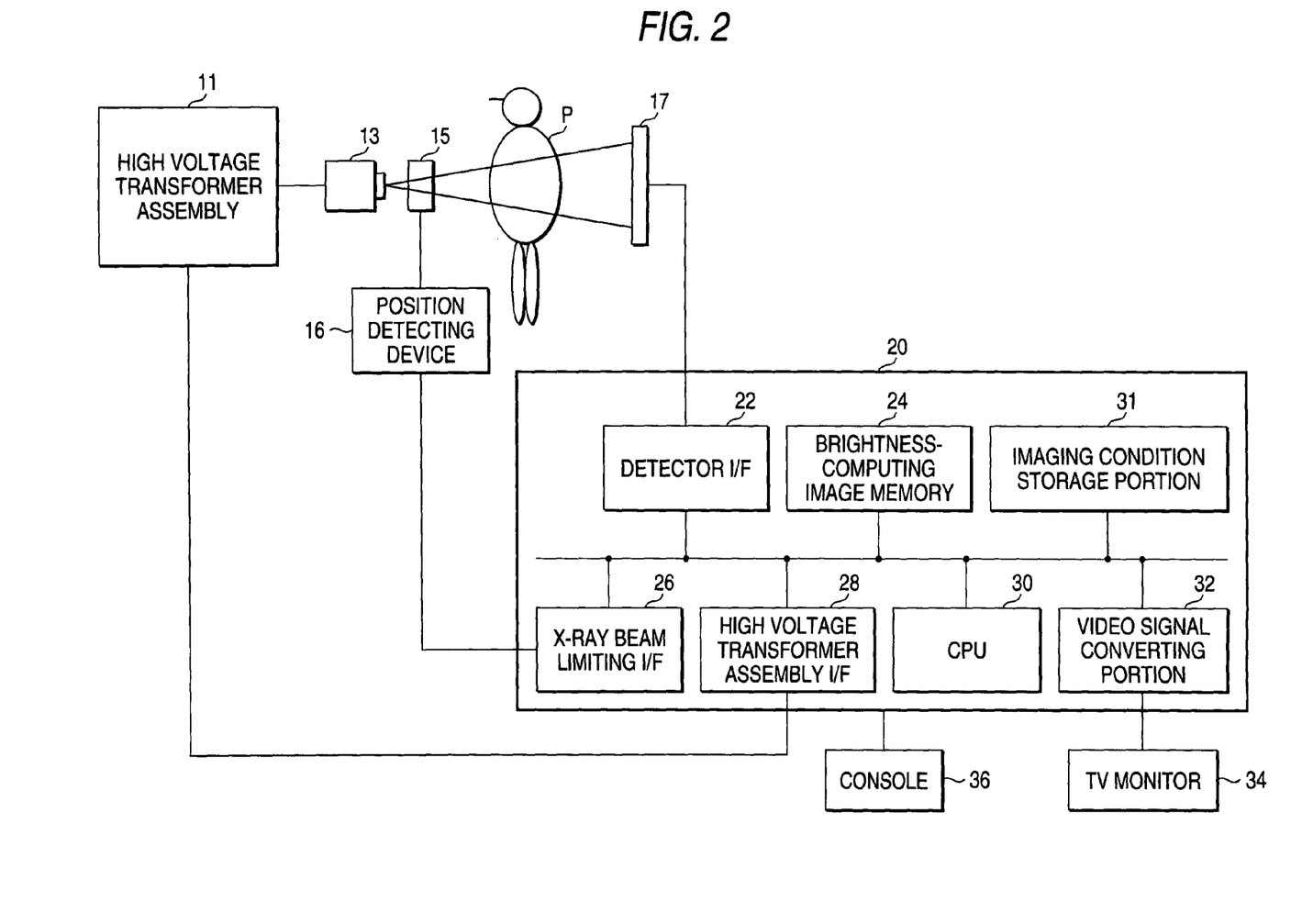
FIG. 2 is a view schematically showing an arrangement of a diagnostic X-ray system according to one embodiment.

FIG. 2 is a view schematically showing an arrangement of a diagnostic X-ray system according to this embodiment.

Referring to FIG. 2, the diagnostic X-ray system comprises a high voltage transformer assembly 11, an X-ray tube 13, an X-ray beam limiting device 15, a detector 17, and a fluoroscopic image processing device 20 provided with a detector interface 22, a brightness-computing image memory 24, an X-ray beam limiting interface 26, a high voltage transformer assembly interface 28, a CPU 30, an imaging condition storage portion 31, and a video signal converting portion 32, as well as a TV monitor 34 and a console 36 both connected to an apparatus main body.

Referring to FIG. 2, the high voltage transformer assembly 11 is a device that supplies the X-ray tube 13 with a high voltage.

The X-ray tube 13 is an X-ray generating vacuum tube that generates an X-ray by accelerating electrons using a high voltage generated in the high voltage transformer assembly 11 to undergo collision with a target.

The X-ray beam limiting device 15 is provided. between the X-ray tube 13 and a subject, and it shapes an X-ray beam radiated from an X-ray focal spot of the X-ray tube 13 into a cone shape and thereby generates an X-ray beam having a required solid angle.

A position detecting device 16 detects position information related to the beam limiting by the X-ray beam limiting device 15 and sends the same to the CPU 30 through the X-ray beam limiting I/F 26. More concretely, it detects a size of a region on which the beam limiting device 15 shapes an X-ray, a distance from the beam limiting device 15 to the detector 17, etc., and sends the detection results to the CPU 30 as the position information.

It should be noted that a distance from the beam limiting device 15 to the detector 17 is not necessarily detected by the position detecting device 16, and it may be arranged in such a manner that the distance is detected and transferred to the CPU 30 by another detector.

The detector 17 detects X-ray transmission data of X-rays passing through the subject P and outputs the same to the detector interface 22. A detector generally includes a flat detector using a semiconductor device, and a detector comprising an X-ray image intensifier and an optical system. The diagnostic X-ray system of the invention may use either detector, and a flat detector is used in this embodiment for ease of explanation.

The detector interface 22 receives digital fluoroscopic image data converted into a digital form in the detector 17, and transfers the data to the CPU 30, the brightness-computing image memory 24, etc.

The brightness-computing image memory 24 receives the digital fluoroscopic image data from the detector interface 22, and stores the same frame by frame.

The X-ray beam limiting interface 26 converts a control signal from the CPU 36 into a predetermined signal sequence and sends the same to the X-ray beam limiting device 15.

The high voltage transformer assembly interface 28 is an interface that transfers a control signal sent from the CPU 30 for generation of an X-ray to the high voltage transformer assembly 11.

The CPU 30 is a central processor that controls acquisition of X-ray fluoroscopic image data and image processing of acquired image data. The CPU 30 also controls: brightness computation for X-ray fluoroscopic image data stored in the brightness-computing image memory 24; changing of a brightness measuring region based on the beam limiting position information inputted from the X-ray beam limiting device 15; determination of X-ray loading factors based on the computed brightness; feedback of the X-ray loading factors to the high voltage transformer assembly 11, etc.

Further, the CPU 30 estimates X-ray loading factors for imaging from the X-ray loading factors for fluoroscopy based on the information stored in the imaging condition storage portion 31. The content of the estimating processing will be explained concretely in automatic imaging condition estimating processing described below.

The imaging condition storage portion 31 stores information related to a pre-defined correspondence between the X-ray loading factors for fluoroscopy and the X-ray loading factors for imaging. For example, the correspondence is determined as follows.

That is, a plurality of phantoms each having a different thickness are prepared and the respective phantoms are subjected to imaging. During the imaging for each phantom, the X-ray loading factors for imaging corresponding to the X-ray loading factors for fluoroscopy are set so that an optimal brightness signal can be obtained on the TV monitor 34. These actually measured values are turned into a table, graph, etc. to be used later as information related to the correspondence. It should be noted that a plurality of phantoms each having a different thickness are prepared by taking it into account that the constitution varies from subject to subject. Also, each phantom has regions each having a different thickness. This is because a consideration is given to the fact that regions of a patient, such as the body and the head, differ in thickness. The correspondence of the X-ray loading factors between those for fluoroscopy and those for imaging is discussed in detail, for example, in U.S. Pat. No. 4,985,908.

The video signal converting portion 32 converts a signal sequence of the input X-ray fluoroscopic image data into a signal in a video format.

The TV monitor 34 displays image data outputted from the video signal converting portion.

The console 36 is an input device provided with a keyboard, various switches, a mouse, etc.

(Automatic Brightness Control Processing)

An explanation will now be given to diagnosis through fluoroscopy as an example of automatic brightness control processing when an X-ray beam limiting manipulation is performed on the diagnostic X-ray system arranged as above, with reference to FIG. 3 and FIG. 4.

The automatic brightness control processing is a control method, by which the X-ray loading factors are set again so that adequate brightness will be given to average brightness related to a reference region within an X-ray fluoroscopic image, and fed back to the high voltage transformer assembly 11. The X-ray loading factors include an X-ray tube current, an X-ray tube voltage, etc.

Figure 3:
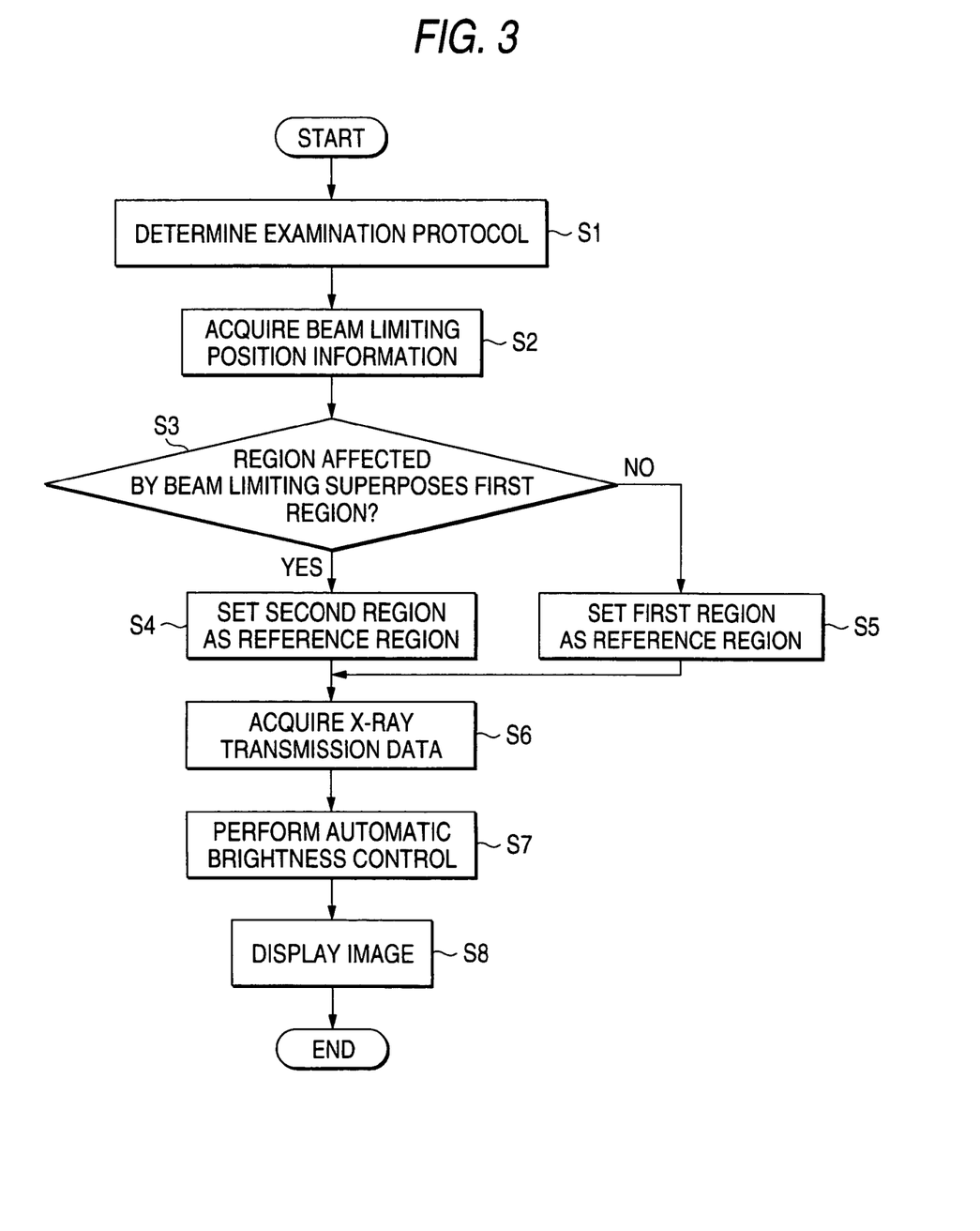
FIG. 3 is a flowchart detailing one example of a procedure for automatic brightness control in which a brightness measuring region can be changed as needed.

FIG. 3 is a flowchart detailing one example of a procedure for automatic brightness control in which a brightness measuring region can be changed as needed, which is one of the characteristics of the diagnostic X-ray system of the invention.

Figure 4:
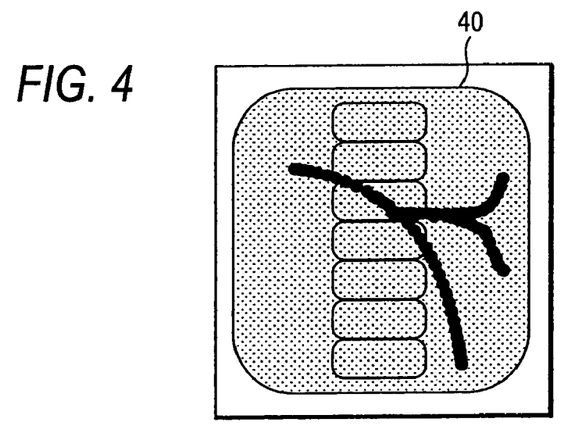
FIG. 4 is a view used to explain automatic brightness control processing related to a first brightness measuring region, showing an X-ray fluoroscopic image displayed on a TV monitor.

FIG. 4 is a view used to explain the automatic brightness control processing, showing an X-ray fluoroscopic image of the backbone displayed on the TV monitor and a region of interest (ROI) of initial setting.

Referring to FIG. 3, an examination protocol is determined first in response to a predetermined input (Step S1). The examination protocol is determined by selecting a region to be examined, etc.

Then, the CPU 30 acquires, from the position information detecting device 16, the position information related to the beam limiting performed by the X-ray beam limiting device 15 (Step S2).

Then, a region affected by the X-ray beam limiting within an image of one frame is computed based on the position information, and a judgment is made as to whether the region thus computed superposes the region of interest of initial setting (hereinafter in this embodiment, referred to as the first brightness measuring region) (Step S3).

To be more specific, given with a size of a region on which an X-ray is shaped by the beam limiting device 15, and a distance from the beam limiting device 15 to the detector 17, an X-ray radiation region on the detector 17 can be specified.

When a judgment is made in Step S3 that the first brightness measuring region 40 superposes the region affected by the beam limiting (see FIG. 8), the flow proceeds to Step S4 to perform processing that changes the reference region related to the automatic brightness control described below, which is one of the characteristics of the system.

Figure 5:
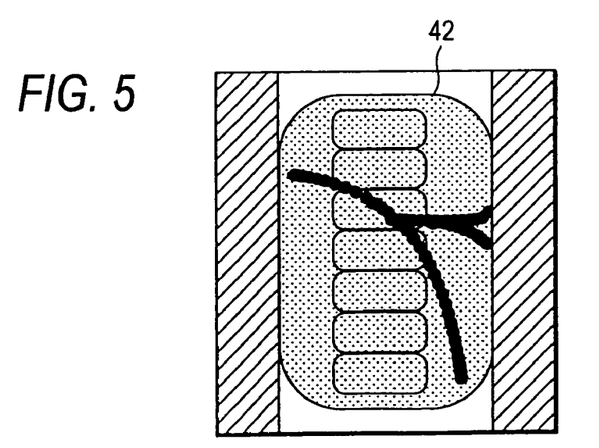
FIG. 5 is a view used to explain automatic brightness control processing when an X-ray beam limiting manipulation is performed, showing an X-ray fluoroscopic image displayed on the TV monitor.

In other words, the CPU 30 changes the first brightness measuring region 40 shown in FIG. 4 to a second brightness measuring region 42 shown in FIG. 5 that is unsusceptible to the beam limiting, based on the region affected by the beam limiting specified in Step S3. Then, the CPU 30 sets the second brightness measuring region 42 as the reference region related to the automatic brightness control (Step S4).

The changed reference region can be found by extracting a region occupied by the X-ray radiation region described in Step S2 within one frame.

On the other hand, when a judgment is made in Step S3 that the first brightness measuring region does not superpose the region affected by the beam limiting, the flow proceeds to Step S3, and the first brightness measuring region 40 is set as the reference region for the automatic brightness control (Step S5).

It should be noted that the first brightness measuring region 40 can be changed into an arbitrary shape through a change manipulation on the console 36. Also, adequate shape, size and the like of the first brightness measuring region 40 differ depending on an object to be imaged (region to be imaged). It is therefore preferable to arrange in such a manner that the first brightness measuring region 40 of adequate shape, size, and the like is set automatically depending on an object to be imaged, the content of which will be described in detail below.

Then, an X-ray is radiated from the X-ray tube 13 at predetermined timing, and the X-ray transmission data of X-rays passing through the subject P is acquired in the detector 17 (Step S6).

Then, the CPU 30 performs the automatic brightness control related to the reference region set in Step S4 or Step S5 (Step S7).

In other words, the acquired X-ray transmission data is stored into the brightness-computing image memory 24 frame by frame through the detector interface 22. The CPU 30 reads out a digital fluoroscopic image of one frame stored in the brightness-computing image memory 24, and computes brightness related to the reference region set in the image thus read out. The brightness computation computes average brightness of all the pixels in the reference region. The CPU 30 then sets X-ray loading factors such that gives adequate brightness to the fluoroscopic image within the reference region, and feeds back the same to the high voltage transformer assembly 11.

As a result of the automatic brightness control described above, an X-ray fluoroscopic image having undergone adequate brightness control is displayed on the TV monitor 34 (Step S8).

According to the procedure as described above, it is possible to display an X-ray fluoroscopic image in adequate brightness by controlling brightness in the best suited manner so as not to be affected by the X-ray beam limiting. It should be noted that the brightness control function can be performed successively. The procedure in this case will now be described briefly.

Figure 6A:
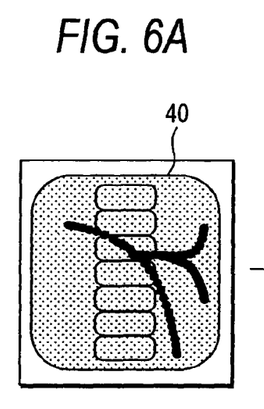
FIG. 6A, FIG. 6B, and FIG. 6C are views used to explain automatic brightness control processing when X-ray beam limiting manipulations are performed successively, each showing an X-ray fluoroscopic image displayed on the TV monitor.
Figure 6B:
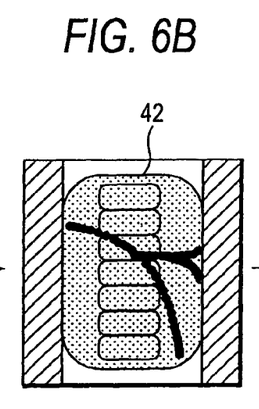
Figure 6C:
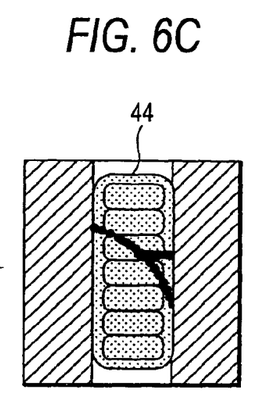

FIG. 6A, FIG. 6B, and FIG. 6C are views used to explain the automatic brightness control processing in a case where X-ray beam limiting manipulations are performed successively.

For example, assume that a beam limiting manipulation is performed for an X-ray fluoroscopic image as shown in FIG. 6A, then a second brightness measuring region 42 as shown in FIG. 6B is set and the automatic brightness control processing is performed based on the region thus set.

When a predetermined beam limiting manipulation is further performed for the fluoroscopic image shown in FIG. 6B, the procedure detailed in FIG. 3 is repeated again. A third brightness measuring region 44 as shown in FIG. 6C is thereby set and the automatic brightness control processing is performed based on the region thus set (in this case, because the examination protocol is not changed, the processing actually starts from Step S2. Further, the judgment in Step S3 and the processing in Step S5 are performed based on the second brightness measuring region 42, and the processing in Step S4 is performed based on the third brightness measuring region 44). It goes without saying that the automatic brightness control processing is performed in the same manner for a beam limiting manipulation or a beam releasing manipulation performed further.

An explanation will now be given to a function that automatically sets a first brightness measuring region for each object to be imaged (region).

Generally, the first brightness measuring region is the region of interest, on which fluoroscopic image information particularly important in diagnosis is displayed. Adequate shape, size, and the like of the region of interest differ depending on an object to be imaged (region to be imaged). It is therefore preferable to set a region corresponding to an object to be diagnosed. To this end, the diagnostic X-ray system of the invention is furnished with a function that automatically sets a region for each object to be imaged. The function will now be explained with reference to FIG. 7.

Figure 8:
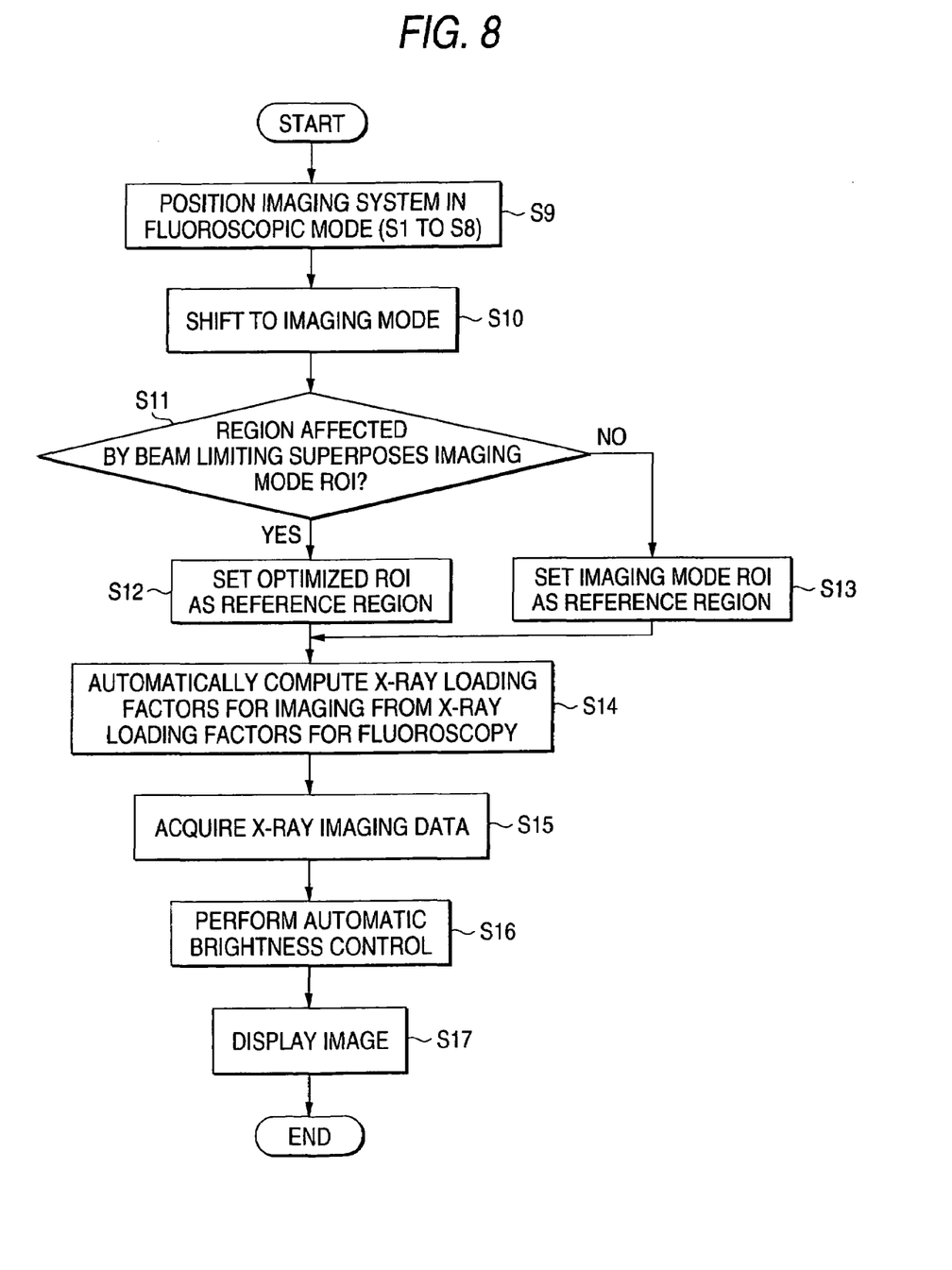
FIG. 8 is a flowchart used to explain a series of imaging operations by the diagnostic X-ray system with automatic imaging condition estimating processing.

FIG. 8 is a view used to explain the function that automatically sets the brightness measuring region for each region.

Referring to FIG. 7, an examination protocol 50 is determined by selecting a region to be examined, etc. as described above, and for example, is classified into a head protocol, an abdomen protocol, a legs protocol, etc. The CPU 30 makes a judgment in Step S3 of FIG. 3 using the first brightness measuring regions 40 pre-registered for each region, based on the examination protocol determined in Step S1 of FIG. 3. FIG. 7 shows examples of the first brightness measuring region corresponding to respective regions. It is obvious that a shape and a size of the respective regions can be changed arbitrarily by changing the content of registration.

According to the arrangement described above, advantages as follows can be achieved.

Because the automatic brightness control is conventionally performed across a brightness measuring region including a region affected by the beam limiting and a region unsusceptible to the beam limiting as shown in FIG. 1, the brightness control has not been performed adequately.

On the contrary, according to the diagnostic X-ray system of the invention, the first brightness measuring region 40 used as the reference region is changed to the second brightness measuring region 42 that is unsusceptible to the beam limiting as shown in FIG. 6, and brightness can be thereby controlled readily and adequately without being affected by the beam limiting. It is thus possible to provide an adequate and easy-to-see X-ray fluoroscopic image.

Also, because the automatic brightness control is performed as needed, an adequate and easy-to-see X-ray fluoroscopic image can be readily provided in real time when an X-ray beam limiting manipulation is performed.

Further, because a brightness measuring region suited for each region to be examined is automatically set, brightness suited for observation of a specific region can be provided. It is thus possible to enhance efficiency by omitting the processing needed to change the reference region.

(Automatic Imaging Condition Estimating Processing)

Automatic imaging condition estimating processing performed by the diagnostic X-ray system will now be explained.

Generally, the diagnostic X-ray system can pick-up an image both in an imaging mode of acquiring detailed still images or moving images of a subject to be diagnosed, and in a fluoroscopic mode of acquiring a series of X-ray images successively or periodically so as to display visible images in real time. When compared with each other, image pick-up in the imaging mode and image pick-up in the fluoroscopic mode are different in size of ROIs of initial setting, in strength of radiated X-rays, etc. More specifically, because the ROI of initial setting in the imaging mode is a region including a subject to be imaged, it is generally larger in size than the ROI of initial setting in the fluoroscopic mode (that is, the first brightness measuring region described above). On the contrary, because images are often observed while an imaging system is being moved to be positioned in the practical fluoroscopic mode, the first brightness measuring region is often set in the vicinity of the center of a frame image (it should be noted that the first brightness measuring region shown in FIG. 4, for example, is shown as a relatively large region for ease of explanation). Also, strength of radiated X-rays in the imaging mode of acquiring diagnosis images is higher than that in the fluoroscopic mode aimed at positioning.

As one configuration of image acquisition using the foregoing, for example, a diagnosis image may be picked up in the imaging mode after the imaging system (the X-ray tube 13, the X-ray beam limiting device 15, the detector 17, an unillustrated C-arm in which these components are installed, etc.) is adequately positioned in the fluoroscopic mode. In this case, because various conditions are different between these modes as described above, all the conditions are reset in a general diagnostic X-ray system when shifting to the imaging mode from the fluoroscopic mode. Hence, conditions have to be set newly for the imaging mode when the imaging mode is started. In general, for example, the imaging conditions are found and set based on first X-ray radiation in the imaging mode.

On the contrary, according to this diagnostic X-ray system, when a diagnosis image is picked up in the imaging mode after the imaging system is adequately positioned in the fluoroscopic mode, the automatic imaging condition estimating processing is performed, which allows information acquired in the fluoroscopic mode to be used in the imaging mode. According to the automatic imaging condition estimating processing, adequate imaging conditions have been set by the time X-rays are radiated in the imaging mode for the first time, and X-ray diagnosis images can be therefore acquired promptly.

FIG. 8 is a flowchart used to explain a series of imaging operations in this diagnostic X-ray system with the automatic imaging condition estimating processing.

Referring to FIG. 8, the imaging system is first positioned in the fluoroscopic mode according to the procedure detailed in FIG. 3 (Step S9). Assume that the processing in Step S1 through Step S8 described above is performed in this step.

Then, the mode is shifted to the imaging mode in response to a predetermined input from the operator through the console 36 (Step S10).

After the mode is shifted to the imaging mode, the CPU 30 judges whether a region affected by the X-ray beam limiting within an image of one frame, which is computed in Step S3 of FIG. 3, superposes the ROI of initial setting in the imaging mode (hereinafter, referred to as the imaging mode ROI) (Step S11).

When it is judged in Step S11 that the imaging mode ROI superposes the region affected by the beam limiting (see FIG. 1), the flow proceeds to Step S12, in which the imaging mode ROI is changed to an optimized ROI that does not superpose the region affected by the beam limiting and then set as the reference region.

To be more specific, the CPU 30 changes, for example, the imaging mode ROI (first brightness measuring region) shown in FIG. 4 to the optimized ROI (second brightness measuring region) unsusceptible to the beam limiting shown in FIG. 5, based on the region affected by the beam limiting specified in Step S3. The CPU 30 then sets the optimized ROI as the reference region related to the automatic brightness control (Step S12).

The optimized ROI can be specified by computing a region occupied by the X-ray radiation region described in Step S2 within one frame as with the second brightness measuring region 42.

On the other hand, when it is judged in Step S11 that the imaging mode ROI does not superpose the region affected by the beam limiting, the flow proceeds to Step S13, and the imaging mode ROI is set as the reference region (Step S13).

Then, the X-ray loading factors in the imaging mode are automatically computed from the X-ray loading factors in the fluoroscopic mode (Step S14). In other words, the X-ray loading factors in the imaging mode are acquired without radiating X-rays, and instead by using information, such as the position of the beam limiting and an optimal brightness value, acquired in the fluoroscopic mode. To be more concrete, the CPU 30 acquires the X-ray loading factors in the imaging mode from the X-ray loading factors for the fluoroscopy performed in Step S9 without the need to radiate X-rays, based on the information related to the correspondence between the X-ray loading factors for fluoroscopy and the X-ray loading factors for imaging stored in the imaging condition storage portion 31. A method of acquiring the X-ray loading factors in the imaging mode from the X-ray loading factors in the fluoroscopic mode is discussed in detail, for example, in U.S. Pat. No. 4,985,908 supra.

Then, X-rays are radiated from the X-ray tube 13 at required timing, and the X-ray imaging data of X-rays passing through the subject P is acquired in the detector 17 (Step S15).

The CPU 30 then performs the automatic brightness control for the reference region set in Step S12 or Step S13 (Step S16). The explanation of the automatic brightness control is given above.

As a result of the automatic brightness control described above, an X-ray imaging image having undergone adequate brightness control can be displayed on the TV monitor 34 (Step S17).

According to the automatic imaging condition estimating processing described above, in a case where positioning processing of the imaging system is performed in the fluoroscopic mode followed by image pick-up of a diagnosis image in the imaging mode, the ROI can be optimized using beam limiting position information acquired in the positioning processing of the imaging system in the preceding step. In other words, although the ROI of initial setting in the imaging mode is larger than the ROI in the fluoroscopic mode, adequate automatic brightness control can be performed in the imaging mode from the initial X-ray irradiation by using the information acquired in the fluoroscopic mode. Hence, according to the diagnostic X-ray system, not only can an adequate and easy-to-see X-ray imaging image be picked up, but also efficiency of diagnosis work can be enhanced because it is no longer necessary to acquire the beam limiting position information again in the imaging mode.

While the embodiments of the invention have been described, it should be appreciated that anyone skilled in the art can achieve various modifications and adjustments within the scope of the invention, and it is understood that such modifications and adjustments are included in the invention. For example, the invention can be modified without changing the gist of the invention as follows.

For instance, in a case where an X-ray beam limiting position is changed at arbitrary timing as an interrupting manipulation in any of the steps of the flow shown in FIG. 3 or FIG. 8, it may be arranged in such a manner that the flow returns to Step S1, so that the processing is performed based on the new X-ray beam limiting position information.

Also, it should be appreciated that the respective embodiments can be combined as needed when possible, and combined effects can be achieved in such a case. Further, the embodiments described above include inventions at various stages, and a variety of inventions can be extracted by adequately combining a plurality of constituent features disclosed above. For example, of all the constituent features shown in the embodiments, even when some constituent features are omitted, the object discussed in the "Problems that the Invention is to Solve" column can be achieved, and in a case where at least one of the advantages described in the "Advantage of the Invention" column is achieved, the arrangement that omits some constituent features can be extracted as an invention.

According to the invention, adequate brightness control processing unsusceptible to X-ray beam limiting and corresponding to a region to be examined can be readily performed.

What is claimed is:

1. A diagnostic X-ray system configured to operate in a fluoroscopy mode and an imaging mode, comprising:
    an X-ray generating unit configured to perform a first X-ray radiation in the fluoroscopy mode to determine an imaging position, and to perform a second X-ray radiation in the imaging mode to acquire a diagnosis image, according to predetermined respective X-ray loading factors, wherein a strength of radiated X-rays in the imaging mode is higher than a strength of radiated X-rays in the fluoroscopy mode;
    an X-ray beam limiting unit configured to limit a radiation region of X-rays through beam limiting;
    an image generating unit configured to generate an image based on the X-rays passing through a subject;
    a region setting unit configured to set a first region in the image when the X-ray system is in the fluoroscopy mode, and to set a second region broader than the first region in the image when the X-ray system is in the imaging mode;
    a region transform unit configured to transform the first region to exclude the radiation region corresponding to the beam limiting when the first region includes the radiation region corresponding to the beam limiting, and to transform the second region to exclude the radiation region corresponding to the beam limiting when the second region includes the radiation region corresponding to the beam limiting;
    a brightness computing unit configured to compute a brightness value within the transformed first region or within the transformed second region when the first region or the second region is transformed by the region transform unit, and to compute a brightness value within the first region or within the second region set by the region setting unit when the first region or the second region is not transformed by the region transform unit; and a controller configured to determine the X-ray loading factor related to the first X-ray radiation or the second X-ray radiation based on the computed brightness value, and to perform feedback control of the X-ray generating unit based on the determined X-ray loading factor.

2. The diagnostic X-ray system according to claim 1, wherein:

the X-ray generating unit is configured to perform the first X-ray radiation with an X-ray intensity lower than that of the second X-ray radiation when the diagnostic X-ray system is operating in the imaging mode, the region setting unit is configured to set the second region in the image when the diagnostic X-ray system is operating in the imaging mode, and the controller is configured to determine the X-ray loading factor related to the second X-ray radiation based on the computed brightness value within the transformed second region corresponding to the first X-ray radiation or the computed brightness value within the second region set by the region setting unit when the diagnostic X-ray system is operating in the imaging mode.

3. The diagnostic X-ray system according to claim 1, wherein the region setting unit is configured to set the first region and the second region in a shape and a size corresponding to a region to be diagnosed.

4. The diagnostic X-ray system according to claim 3, wherein the brightness computing unit is configured to perform the brightness computation related to the first region or the second region in real time in association with the beam limiting manipulation by said beam limiting unit, and the controller is configured to perform the feedback control of an X-ray loading factor based on the first region or the second region in real time in association with the beam limiting manipulation by said beam limiting unit.

5. The diagnostic X-ray system according to claim 1, wherein the brightness computing unit is configured to perform the brightness computation related to the first region or the second region in real time in association with the beam limiting manipulation by said beam limiting unit, and the controller is configured to perform the feedback control of an X-ray loading factor based on the first region or the second region in real time in association with the beam limiting manipulation by said beam limiting unit.

6. A diagnostic X-ray system configured to operate in a fluoroscopy mode and an imaging mode, comprising:

an X-ray generating unit configured to perform a first X-ray radiation in the fluoroscopy mode to determine an imaging position, and a second X-ray radiation in the imaging mode to acquire a diagnosis image, according to predetermined respective X-ray loading factors, wherein a strength of radiated X-rays in the imaging mode is higher than a strength of radiated X-rays in the fluoroscopy mode;

an X-ray beam limiting unit configured to limit a radiation region of the X-rays through beam limiting;

an image generating unit configured to generate an image based on the X-rays passing through a subject;

a region setting unit configured to set a first region in the image when the X-ray system is in to the fluoroscopy mode, and to set a second region broader than the first region in the image when the X-ray system is in the imaging mode;

a region transform unit configured to transform the first region to exclude the radiation region corresponding to the beam limiting when the first region includes the radiation region corresponding to the beam limiting, and to transform the second region to exclude the radiation region corresponding to the beam limiting when the second region includes the radiation region corresponding to the beam limiting;

a brightness computing unit configured to compute a brightness value within the transformed first region or within the transformed second region when the first region or the second region is transformed by the region transform unit, and to compute a brightness value within the first region or within the second region set by the region setting unit when the first region or the second region is not transformed by the region transform unit; and a controller configured to determine the X-ray loading factor related to the second X-ray radiation, based on the brightness value within the transformed second region corresponding to the first X-ray radiation or the brightness value within the second region set by the region set unit, and to perform feedback control of the X-ray generating unit based on the determined X-ray loading factor.

7. The diagnostic X-ray system according to claim 6, wherein the region setting unit is configured to set the first region and the second region in a shape and a size corresponding to a region to be diagnosed.

8. The diagnostic X-ray system according to claim 7, wherein the brightness computing unit is configured to perform the brightness computation related to the first region or the second region in real time in association with the beam limiting manipulation by said beam limiting unit, and the controller is configured to perform the feedback control of an X-ray loading factor based on the first region or the second region in real time in association with a beam limiting manipulation by said beam limiting unit.

9. The diagnostic X-ray system according to claim 6, wherein the brightness computing unit is configured to perform the brightness computation related to the first region or the second region in real time in association with the beam limiting manipulation by said beam limiting unit, and the controller is configured to perform the feedback control of an X-ray loading factor based on the first region or the second region in real time in association with a beam limiting manipulation by said beam limiting unit.

* * * * *